United States Patent [19]

Nathanson

[11] 4,094,316
[45] June 13, 1978

[54] ADHESIVE BANDAGE WITH REUSABLE APPLIQUE

[76] Inventor: Eric Nathanson, 2618 Batchelder St., Brooklyn, N.Y. 11235

[21] Appl. No.: 717,600

[22] Filed: Aug. 26, 1976

[51] Int. Cl.² ............... A61L 15/00; A41H 27/00; B32B 35/00
[52] U.S. Cl. ................................ 128/156; 156/94; 428/63
[58] Field of Search ............ 128/132 R, 155, 156; 156/94; 428/63

[56] References Cited
U.S. PATENT DOCUMENTS

| 2,823,672 | 2/1958 | Schladermundt | 128/156 |
| 2,836,178 | 5/1958 | Barr | 128/155 |
| 2,905,174 | 9/1959 | Smith | 128/156 |

Primary Examiner—Robert W. Michell
Assistant Examiner—Jerome D. Stremcha
Attorney, Agent, or Firm—Robert W. Fiddler

[57] ABSTRACT

A combined adhesive bandage and applique in which a selectively removable applique is applied to the adhesive backing strip of an adhesive bandage serving the threefold function of 1) increasing the attractiveness of the bandage; 2) providing a decorative applique for reuse as desired; or 3) providing a clothing repair patch. The bandage-applique combination comprises an applique formed with a reusable adhesive surface on one side thereof releasably adhered to a release liner which is adhered to an adhesive coating on the top of an adhesive bandage tape having a lower adhesive coating to which a bandage pad is adhered at the central portion of the tape with a removable protective sheet covering the bandage strip adhesive and bandage.

7 Claims, 3 Drawing Figures

ADHESIVE BANDAGE WITH REUSABLE APPLIQUE

BACKGROUND OF THE INVENTION

This invention relates to the art of adhesive bandages, and more particularly to an improved adhesive bandage formed with a reusable applique serving the threefold function of 1) increasing the attractiveness of the bandage; 2) providing an applique which may be reused for decorative and ornamental purposes; and/or 3) providing a clothing repair patch.

Adhesive bandages of the type sold under the trademark BAND-AID have been widely utilized in which a bandage pad of gauze or the like absorbent material is positioned at the center of a strip of adhesive tape, so that in use the bandage pad may be positioned over a wound with the tape secured to the adjacent skin surface to maintain the pad in desired position. Where these adhesive bandages are applied by a user to an exposed surface of the body such as on the face, or on the hands, the appearance of the adhesive bandage has often been regarded as unsightly. Attempts have been made to minimize the unsightliness of the bandage by tinting the adhesive tape to match the skin.

Additionally, such bandages have been made for use by children with the tape provided with a decorative imprint, so as to enhance the attractiveness thereof.

However, notwithstanding the attempts to increase the attractiveness of such adhesive bandages, there still exists a problem in encouraging the use of such bandages for their desired protective function when necessary, particularly by children.

BRIEF DESCRIPTION OF THE INVENTION

It is with the above problems and considerations in mind that the present improved adhesive bandage combined with an applique has been evolved with a view to increasing the acceptability of the use of the adhesive bandage, particularly on exposed skin areas, and further to increase the utility of the adhesive bandage by permitting subsequent use of a portion thereof for a decorative applique, or as a clothing repair patch.

Further, by providing a reusable decorative applique in combination with the adhesive bandage, it is contemplated that the decorative applique may be imprinted with advertising indicia, so that various commercial enterprises might be induced to provide such adhesive bandages with decorative appliques at little or no cost to the consumer, thereby reducing consumer costs. Consumer costs may further be reduced by providing the user with a clothing repair patch which many consumers now purchase as a separate item.

It is accordingly among the primary objects of the invention to provide an improved adhesive bandage with a desired decorative appearance, and with increased utility.

A further object of the invention is to provide an improved adhesive bandage with a portion thereof suitable for use as a decorative applique, and/or a repair patch.

An additional object of the invention is to provide a combined applique and adhesive bandage which may readily be fabricated by conventional adhesive bandage forming equipment and techniques.

Another object of the invention is to provide a combined decorative applique and adhesive bandage in which the applique is subject to reuse for advertising purposes.

These and other objects of the invention which will become hereafter more apparent are achieved by providing an applique formed of any sheet material, preferably having a desired textile weave pattern, such for example as denim, or formed of a fabric, with a desired print thereon. One surface of the applique is provided with a reusable adhesive, preferably of a pressure sensitive type, and this adhesive backed applique surface is adhered to a so-called "release liner" formed of waxed or other coated paper, vinyl, or the like, which though adhering to the adhesive on the applique has a bond strength with respect to the adhesive lower than that with which the applique adheres to the adhesive. The adhesive surface of the liner is then adhered to the top (or non-bandage carrying surface) of the adhesive tape forming the adhesive bandage, and having a bandage pad at the center of the adhesive tape, with a protective sheet underlying the adhesive portion of the tape and the bandage.

In use, the above described assembly is encased in a sterile wrapper, as is conventional for the distribution of adhesive bandages. The user, after removing the assembly from the package, removes the protective sheet from the adhesive surface of the tape, exposing the bandage pad and adhesive surface. The bandage pad is then positioned over the area to be protected, and the adhesive surface of the tape is secured to the surrounding skin to hold the pad in desired position, in conventional fashion. The applique topping on the bandage has been provided either to match the clothing worn, or to provide any desired esthetic effect desired, or carry any desired promotional imprint. After the bandage has served its wound protecting function, the applique is removed from the release liner and may thereafter be applied where desired, as for example as a decorative patch on clothing, or as an ornamental or repair patch in any other area desired.

A feature of the invention resides in the ability to match the appearance of the adhesive bandage to the esthetic tastes of the user, so that those caught up in the current denim rage may readily obtain adhesive bandages with a denim applique.

Another feature of the invention resides in the fact that the decorative applique increases the utilization of the adhesive bandage by permitting use of the applique for subsequent decorative effects where desired, for promotional purposes, or as a repair patch.

BRIEF DESCRIPTION OF THE DRAWINGS

The specific details of a preferred embodiment and the best mode contemplated for carrying out a preferred embodiment of the invention, and of the manner and process of making and using same, will be described in full, clear, concise and exact terms in conjunction with the accompanying drawings, wherein.

DESCRIPTION OF PREFERRED EMBODIMENT OF THE INVENTION

Figure 1:
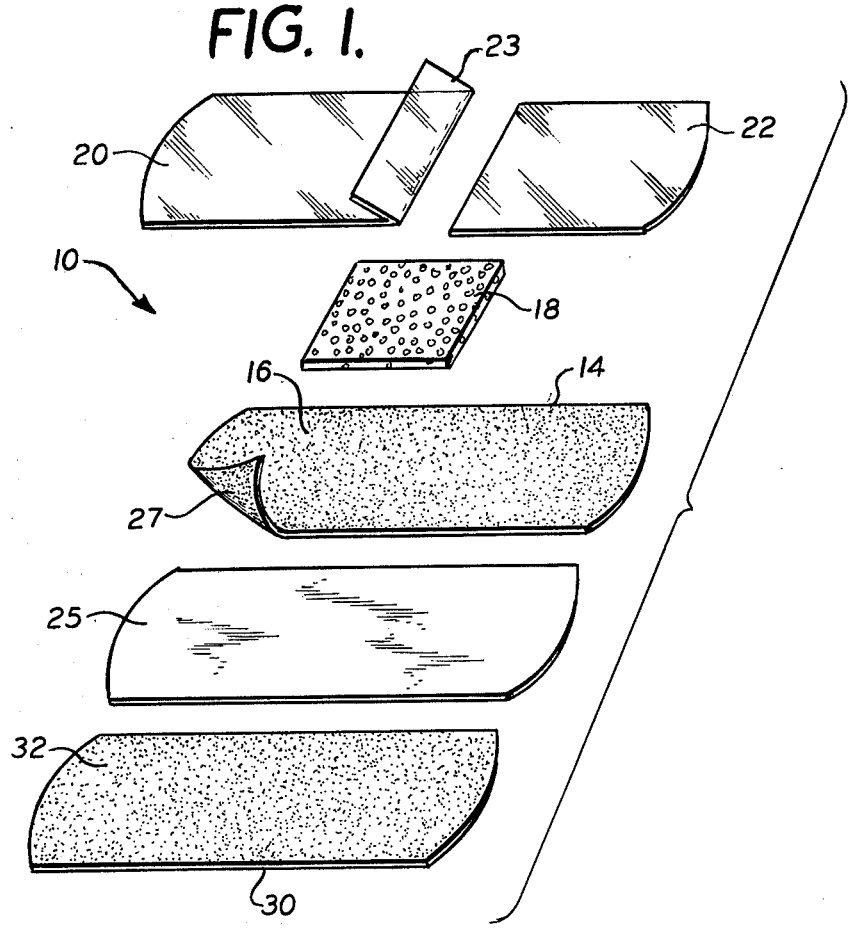
FIG. 1 is an exploded perspective view showing the component parts of the combined adhesive bandage and applique.

Referring now more particularly to the drawings, where like numerals in the various FIGS. will be employed to designate parts, as seen in the drawings, the adhesive bandage applique generally designated 10 comprises a strip of adhesive tape 14 formed of conventional sheet material as generally employed for surgical tape, such as woven textile fabrics, or sheet plastics. In the illustrated embodiment, both surfaces of the tape are coated with a pressure sensitive reusable adhesive. One surface of this tape 14 is coated with an adhesive 16, as shown uppermost in FIG. 1, and lowermost in FIGS. 2 and 3. Secured to the adhesive surface 16, at the center of tape 14, is a bandage pad 18 formed of gauze, a felted material, or any one of a wide variety of absorbent materials conventionally employed in the formation of bandages.

Figure 2:
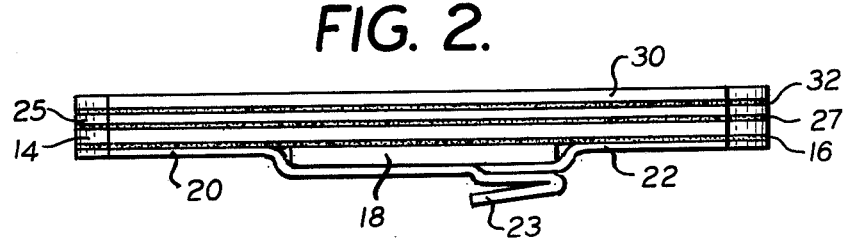
FIG. 2 is a cross-sectional view along a longitudinal axis of the adhesive bandage applique combination.
Figure 3:
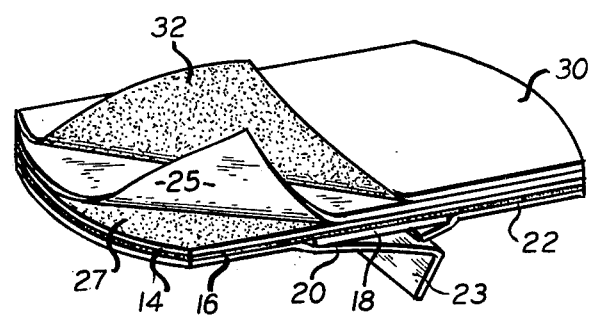
FIG. 3 is a perspective view of the adhesive bandage applique combination showing the component parts thereof in a partially separated position as they would be separated for use.

A protective sheet is provided to cover the exposed adhesive 16 on tape 14 adjacent the bandage pad 18, and to cover the bandage pad 18. This sheet is formed preferably in two parts, 20 and 22, with protective sheet part 20 provided with a reverse bent finger tab 23. Sheet part 20 with reverse bent finger tab 23 is formed of a size to extend from one end of tape 14 over the bandage pad 18, as best seen in FIG. 2. Protective sheet portion 22 is formed of a size to extend from the opposite end of tape 14, as viewed in FIG. 2, to a point beneath the folded over free end of finger tab 23.

A release liner 25 is provided, which as typical of such known release liners, is formed of a sheet material having a relatively smooth surface which will bond to an adhesive with a bond strength relatively weaker than the bond strength between the tape or applique material and the adhesive. Sheet materials such as waxed or otherwise coated or calendered paper, or plastic sheeting may be satisfactorily employed. In the illustrated embodiment, release liner 25 is secured to the adhesive coating 27 on the face of tape 14, opposite to the bandage bearing surface of the tape. It will, however, be understood by those skilled in the art that the release liner may be formed with only one release surface, as by waxing, coating or calendering only one surface of the sheet forming the release liner. With such release liner, the non-release surface of the liner may be formed with an adhesive layer which may be adhered to the tape 14, which is in this arrangement formed with adhesive only on the bandage carrying surface of tape 14.

Overlying the release liner 25 is an applique 30, which may be selectively formed of any one of a wide variety of decorative sheet materials such as textile fabrics, sheet plastics, felted sheeting, or any one of the wide variety of flexible sheet materials, such as might desirably be employed in the formation of appliques. By way of illustration, in order to cater to the current fad for the utilization of denim fabrics, the applique layer 30 may suitably be formed of a strip of denim having a surface coated with a reusable adhesive layer 32 which permits releasable securement of the applique 30 to the release liner 25.

A preferred example as illustrated has been formed utilizing the following materials:
protective sheet: 2–4 mil polyvinyl
  adhesive: pressure sensitive acrylic such as AIS 20 provided by Electro Seal Corp. of Maywood, New Jersey
bandage pad: perforated vinyl enclosed felted cotton
adhesive tape: perforated 2 mil vinyl
release liner: parafin coated paper (both sides) 2 mils thick
applique layer: cotton denim

OPERATION

In use, though the above described components may be hand cut and assembled, they are preferably formed by conventionally available adhesive bandage forming equipment with the applique and release sheet preferably stamped simultaneously with the adhesive tape and protective sheet.

After removal of the assembled adhesive bandage and applique from the conventionally employed sanitary packaging, the assembly is employed as adhesive bandages are conventionally employed by peeling the protective sheet away from the bandage pad, applying the pad over the area to be bandaged, and stripping the protective sheet while simultaneously exerting pressure on the adhesive coated portions of the tape adjacent the pad to secure the tape to the skin adjacent the pad covered area.

The user may at this time or after the bandage is to be discarded, selectively remove the applique by peeling same from the release liner, and reapplying the reusable pressure sensitive adhesive backed applique at any other place, as desired.

The applique, as is apparent, may function as a decorative patch on clothing, such as worn by many teenagers, or the applique may be combined with other appliques to form any designs desired. Where advertising promotions are imprinted on the applique, the exposure provided by use of the applique is obviously desirable to the potential advertiser. Further, the applique may be employed as a repair patch, such as many consumers presently purchase to effect repairs of tears or worn spots on clothing.

The above disclosure has been given by way of illustration and elucidation, and not by way of limitation, and it is desired to protect all embodiment of the herein disclosed inventive concept within the scope of the appended claims.

What is claimed is:

1. A combined adhesive bandage and applique comprising:
  an adhesive tape having an adhesive coating on at least one face thereof;
  a bandage pad smaller in area than said tape secured by the adhesive coating to a central portion of said tape;
  a decorative applique clothing patch strip dimensioned of an area substantially congruent to that of said adhesive tape, and formed with a continuous web of material having a pressure sensitive reusable adhesive layer along one entire surface of said web releasably secured with respect to said tape on the side thereof opposed to the side of the tape to which said bandage is secured.

2. A combined adhesive bandage and applique as in claim 1, in which a protective sheet is provided overlying said bandage pad and removably secured to the adhesive coating on said tape bordering said bandage.

3. A combined adhesive bandage and applique as in claim 1 in which a release liner is adhesively secured to said tape on the side thereof opposed to the side of the tape to which said bandage pad is secured and said applique is releasably secured to said liner.

4. A combined adhesive bandage and applique as in claim 1, in which said adhesive tape is coated on opposed faces thereof.

5. A combined adhesive bandage and applique as in claim 1, in which said applique is formed of a sheet material having the appearance of blue denim.

6. A combined adhesive bandage and applique as in claim 1, in which said applique is formed of a woven textile material.

7. A combined adhesive bandage and applique as in claim 1, in which said applique is formed of printed sheet material.

* * * * *